United States Patent
Sakai et al.

(10) Patent No.: US 10,367,979 B2
(45) Date of Patent: Jul. 30, 2019

(54) IMAGE PROCESSING APPARATUS, IMAGING APPARATUS, DRIVER MONITORING SYSTEM, VEHICLE, AND IMAGE PROCESSING METHOD

(71) Applicant: KYOCERA Corporation, Kyoto (JP)

(72) Inventors: Takeshi Sakai, Tokyo (JP); Woojung Kim, Yokosuka (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/748,201

(22) PCT Filed: Jun. 29, 2016

(86) PCT No.: PCT/JP2016/003126
§ 371 (c)(1),
(2) Date: Jan. 29, 2018

(87) PCT Pub. No.: WO2017/017896
PCT Pub. Date: Feb. 2, 2017

(65) Prior Publication Data
US 2018/0227472 A1  Aug. 9, 2018

(30) Foreign Application Priority Data
Jul. 29, 2015 (JP) .................. 2015-150073

(51) Int. Cl.
*A61B 3/11* (2006.01)
*G06K 9/00* (2006.01)
(Continued)

(52) U.S. Cl.
CPC ........... *H04N 5/2256* (2013.01); *A61B 3/112* (2013.01); *B60R 16/02* (2013.01); *G03B 15/00* (2013.01);
(Continued)

(58) Field of Classification Search
None
See application file for complete search history.

(56) References Cited

U.S. PATENT DOCUMENTS 6,542,624 B1 * 4/2003 Oda .................. G06K 9/00597
382/117
7,744,216 B1   6/2010 Uhlhorn
(Continued)

FOREIGN PATENT DOCUMENTS

GB      2495328 A       4/2013
JP      07032907 A  *   2/1995
(Continued)

OTHER PUBLICATIONS

International Search Report issued in PCT/JP2016/003126; dated Aug. 9, 2016.
(Continued)

*Primary Examiner* — Roberto Velez
*Assistant Examiner* — Quan Pham
(74) *Attorney, Agent, or Firm* — Studebaker & Brackett PC (57) ABSTRACT

An image processing apparatus includes an image acquiring unit and a controller. The image acquiring unit acquires a captured image capturing a subject illuminated by light from at least one light source. The controller generates adjustment information for adjusting an intensity of the light from the at least one light source on the basis of a size of a pupil of the subject determined from the captured image.

10 Claims, 7 Drawing Sheets

(51) Int. Cl.
 G08G 1/16 (2006.01)
 B60R 16/02 (2006.01)
 G03B 15/00 (2006.01)
 G03B 15/03 (2006.01)
 G03B 15/05 (2006.01)
 H04N 5/225 (2006.01)
 H04N 5/232 (2006.01)
 H04N 5/238 (2006.01)

(52) U.S. Cl.
 CPC .............. *G03B 15/03* (2013.01); *G03B 15/05* (2013.01); *G06K 9/00604* (2013.01); *G08G 1/16* (2013.01); *H04N 5/225* (2013.01); *H04N 5/232* (2013.01); *H04N 5/238* (2013.01); *H04N 5/23229* (2013.01); *G06K 9/00617* (2013.01)

(56) References Cited

U.S. PATENT DOCUMENTS

2006/0147094 A1\* 7/2006 Yoo .................... G06K 9/00604
 382/117
2015/0294464 A1\* 10/2015 Kim .................... G06K 9/00597
 382/117
2016/0104454 A1\* 4/2016 Huang .................... G09G 5/10
 345/156
2016/0198091 A1\* 7/2016 Edwards ................ G06F 3/013
 348/78

FOREIGN PATENT DOCUMENTS

| | | | |
|---|---|---|---|
| JP | H07-032907 | A | 2/1995 |
| JP | H11-056782 | A | 3/1999 |
| JP | 2009-200718 | A | 9/2009 |
| JP | 2010-176382 | A | 8/2010 |
| JP | 2010176382 | A \* | 8/2010 |

OTHER PUBLICATIONS

Written Opinion issued in PCT/JP2016/003126; dated Aug. 9, 2016; with English language Concise Explanation.

\* cited by examiner

IMAGE PROCESSING APPARATUS, IMAGING APPARATUS, DRIVER MONITORING SYSTEM, VEHICLE, AND IMAGE PROCESSING METHOD

CROSS REFERENCE TO RELATED APPLICATION

This application claims priority to and the benefit of Japanese Patent Application No. 2015-150073 filed on Jul. 29, 2015, the entire contents of which are incorporated herein by reference.

TECHNICAL FIELD

The present disclosure relates to an image processing apparatus configured to monitor a state of a subject such as a driver of a vehicle, an imaging apparatus, a driver monitoring system, the vehicle, and an image processing method.

BACKGROUND

Conventional apparatuses configured to emit light in the infrared band to a subject such as a driver of a vehicle, monitor a state of the subject using a captured image captured by an infrared camera, and generate an alarm to prevent the driver from, for example, falling asleep, as necessary, are known.

SUMMARY

An image processing apparatus according to an embodiment of the present disclosure includes an image acquiring unit and a controller. The image acquiring unit acquires a captured image of a subject illuminated by light from at least one light source. The controller generates adjustment information for adjusting an intensity of the light from the at least one light source on the basis of a size of a pupil of the subject determined from the captured image.

An imaging apparatus according to an embodiment of the present disclosure includes an image sensor and a controller. The image sensor generates a captured image by capturing a subject illuminated by light from a light source. The controller generates adjustment information for adjusting an intensity of the light from the light source on the basis of a size of a pupil of the subject determined from the captured image.

A driver monitoring system according to an embodiment of the present disclosure includes an illumination apparatus, an imaging apparatus, and an image processing apparatus. The illumination apparatus emits light to a driver of a vehicle. The imaging apparatus generates a captured image by capturing the driver illuminated by the light. The image processing apparatus generates adjustment information for adjusting an intensity of the light from the light source on the basis of a size of a pupil of the driver determined from the captured image.

A vehicle according to an embodiment of the present disclosure includes an illumination apparatus, an imaging apparatus, and an image processing apparatus. The illumination apparatus emits light to a driver. The imaging apparatus generates a captured image by capturing the driver illuminated by the light. The image processing apparatus generates adjustment information for adjusting an intensity of the light from the light source on the basis of a size of a pupil of the driver determined from the captured image.

An image processing method according to an embodiment of the present disclosure includes a step of acquiring a captured image capturing a subject using light from a light source; and a step of generating adjustment information for adjusting an intensity of the light from the light source on the basis of a size of a pupil of the subject determined from the captured image.

DETAILED DESCRIPTION

Hereinafter, an embodiment of the present disclosure will be described with reference to the accompanying drawings.

Figure 1:
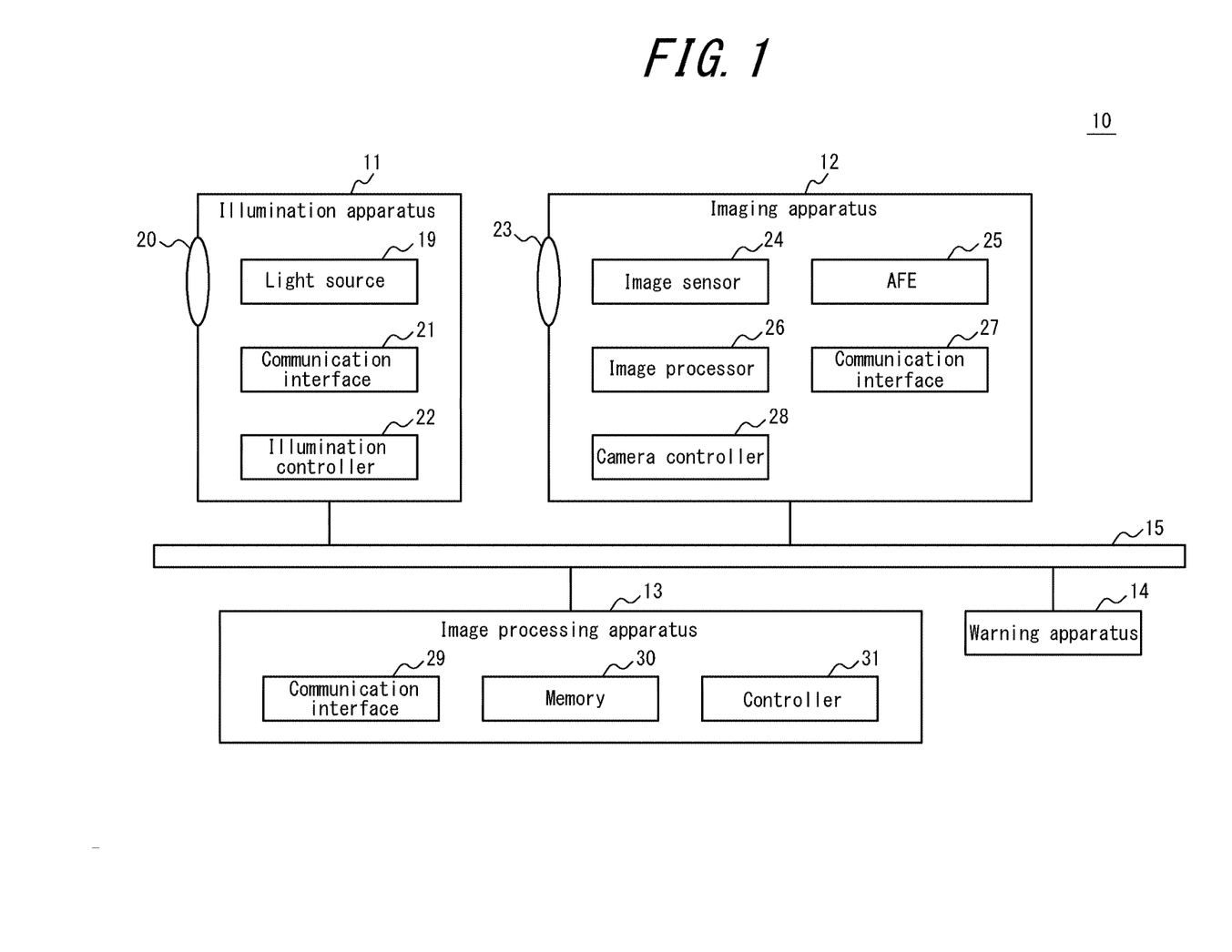
FIG. 1 is a block diagram schematically illustrating a configuration of a driver monitoring system according to an embodiment of the present disclosure.

Referring to FIG. 1, a driver monitoring system according to an embodiment of the present disclosure will be described. The driver monitoring system is mounted in a vehicle. The term "vehicle" used herein may include a car, a ship, an aircraft, and so on. Hereinafter, a car is used as the vehicle by way of example.

As illustrated in FIG. 1, the driver monitoring system 10 includes an illumination apparatus 11, an imaging apparatus 12, and an image processing apparatus 13. The driver monitoring system 10 may optionally include a warning apparatus 14 as well. The constituent elements of the driver monitoring system 10 may exchange information with one another in a wired or wireless manner, or via a network 15 such as a CAN.

Figure 2:
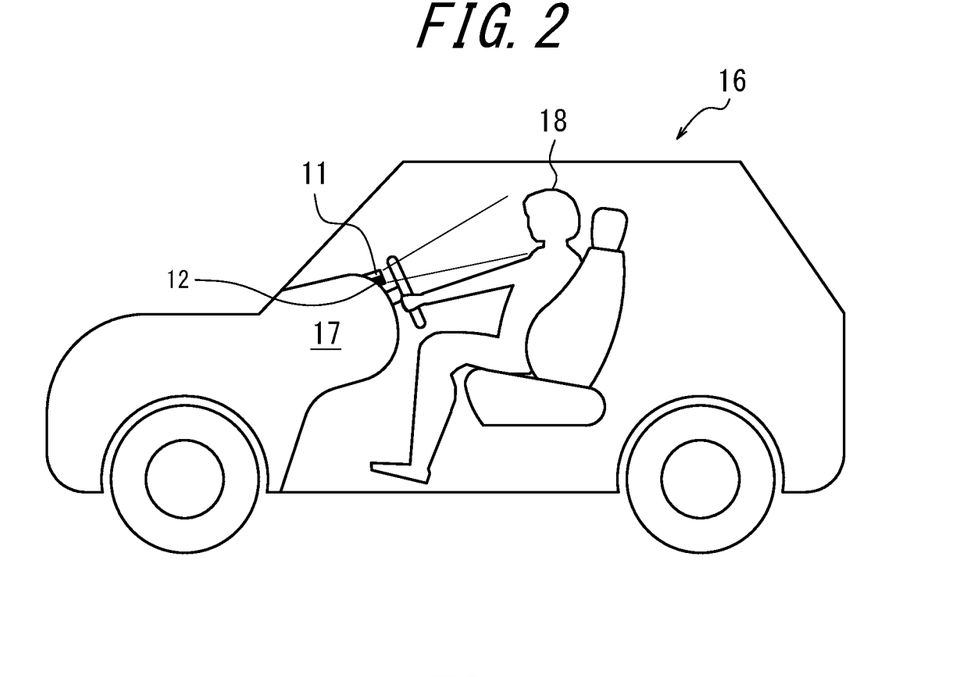
FIG. 2 is a diagram illustrating a schematic view of a vehicle that is provided with the driver monitoring system of FIG. 1.

As illustrated in FIG. 2, the illumination apparatus 11 is mounted on, for example, a dashboard 17 of the car 16 in such a manner as to be able to emit light to a face of a subject 18 such as a driver. The imaging apparatus 12 is mounted on, for example, the dashboard 17 of the car 16 in such a manner as to be able to capture the face of the subject 18 illuminated by the light from the illumination apparatus 11. According to the present embodiment, the illumination apparatus 11 and the imaging apparatus 12 are disposed close to each other. The imaging apparatus 12 generates a captured image (an image of a bright pupil) in which a pupil of an eye of the subject 18 is brightly illuminated.

Configurations of the constituent elements of the driver monitoring system 10 will now be described.

The illumination apparatus 11, as illustrated in FIG. 1, includes at least one light source 19, an illumination optical system 20, a communication interface 21, and an illumination controller 22.

The light source 19 includes, for example, an LED. The light source 19 emits light in a predetermined wavelength band. According to the present embodiment, the light source 19 is an infrared LED configured to emit diffused light in the infrared band. However, the emitted light may be in any appropriate wavelength band and may have any appropriate directionality.

The illumination optical system 20 may include, for example, a lens with an adjusted angle. The illumination optical system 20 emits light that passes through the illumination optical system 20. According to the present embodiment, the light from the light source 19 having passed through the illumination optical system 20 is projected onto the entire face of the subject 18.

The communication interface 21 includes an interface configured to input (acquire) and output information via the network 15.

The illumination controller 22 includes, for example, a dedicated microprocessor, or a general-purpose CPU configured to perform a specific function by reading a specific program. The illumination controller 22 controls operation of constituent elements of the illumination apparatus 11. For example, the illumination controller 22 causes the light source 19 to periodically perform pulse-lighting of the light in the infrared band for a predetermined time period in response to a synchronization signal obtained from the imaging apparatus 12 via the communication interface 21.

To cause the light source 19 to perform the pulse-lighting, the illumination controller 22 uses a pulse signal (a control signal) for causing the light source 19 to perform the pulse-lighting. The intensity of the light emitted from the illumination apparatus 11 varies depending on adjustment parameters such as a duty ratio defined as the product of the pulse width and the reciprocal of the period (a frequency) of the control signal, a value of a driving current (a magnitude of the pulse) of the light source 19, and the number of the light sources 19 configured to perform the pulse-lighting. According to the present embodiment, the illumination controller 22 acquires adjustment information from the image processing apparatus 13 via the communication interface 21. The adjustment information specifies a value of the adjustment parameter used for the adjustment of the intensity of the light emitted from the illumination apparatus 11. The adjustment parameter includes at least one of, for example, the duty ratio of the control signal, the pulse width, the period or the frequency, the value of the driving current of the light source 19, and the number of the light sources 19 configured to emit the light. The illumination controller 22 generates the control signal in accordance with the adjustment information and, by using the control signal, causes the light source 19 to perform the pulse-lighting. Alternatively, the adjustment information itself may include the control signal. In this case, the illumination controller 22 causes the light source 19 to perform the pulse-lighting by using the control signal included in the adjustment information.

The imaging apparatus 12 includes an imaging optical system 23, an image sensor 24, an AFE 25, an image processer 26, a communication interface 27, and a camera controller 28.

The imaging optical system 23 includes an aperture and a plurality of lenses. The imaging optical system 23 forms a subject image. The imaging optical system 23 further includes a filter that transmits only light in a predetermined wavelength band, which is light in the infrared band according to the present embodiment. The imaging optical system 23 is arranged on a housing of the imaging apparatus 12 in such a manner as to enable capture of light from the illumination apparatus 11 which is reflected by an illumination target. According to the present embodiment, the imaging optical system 23 is capable of forming the subject image including the face of the subject 18 illuminated by the light. According to the present embodiment, the imaging optical system 23 is arranged close to the illumination optical system 20 of the illumination apparatus 11.

The image sensor 24 includes, for example, a CCD image sensor or a CMOS image sensor. The image sensor 24 captures the subject image formed by the imaging optical system 23 and generates the captured image. When the image sensor 24 is the CMOS image sensor, the image sensor 24 may be configured as an image sensor having the functions of the AFE 25.

The AFE 25 includes, for example, CDS, AGC, and ADC. The AFE 25 subjects the captured image in an analogue state generated by the image sensor 24 to predetermined pre-stage image processing such as CDS, AGC (gain adjustment), and ADC (A/D conversion).

The image processer 26 includes a processor specialized for image processing such as, for example, a DSP. The image processer 26 subjects the captured image subjected to the pre-stage image processing by the AFE 25 to predetermined post-stage image processing such as exposure adjustment.

The communication interface 27 includes an interface configured to input (acquire) and output information via the network 15.

The camera controller 28 includes a specialized microprocessor, or a general-purpose CPU configured to perform a specific function by reading a specific program. The camera controller 28 performs overall control of the imaging apparatus 12. For example, the camera controller 28 generates a synchronization signal indicating a timing for capturing an image and outputs the synchronization signal to the illumination apparatus 11 via the communication interface 27. The camera controller 28 causes the image sensor 24 to capture the subject image periodically, e.g., at 30 fps. The camera controller 28 controls operation of the image processer 26 and the communication interface 27 such that the captured image subjected to the post-stage image processing is output to the image processing apparatus 13 via the network 15.

The image processing apparatus 13 includes a communication interface 29, a memory 30, and a controller 31.

The communication interface 29 includes an interface configured to input (acquire) and output information via the network 15. The communication interface 29 functions as an image acquiring unit configured to acquire the captured image generated by the imaging apparatus 12.

Figure 3:
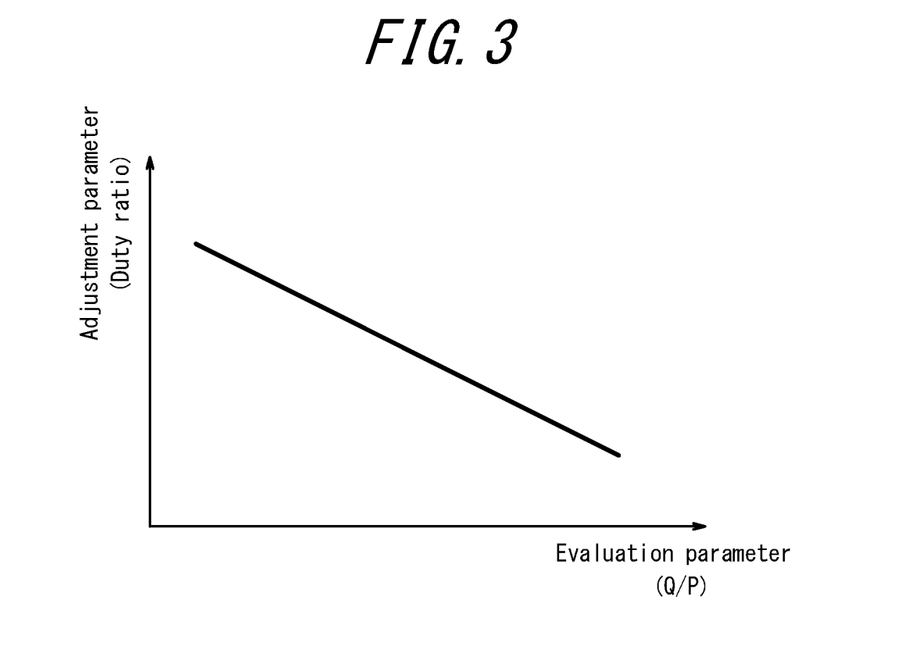
FIG. 3 is a graph illustrating a relation between an adjustment parameter and an evaluation parameter.

The memory 30 stores various information and programs necessary for the operation of the image processing apparatus 13. As illustrated in FIG. 3, for example, the memory 30 stores, in advance, information indicating a correlation between the evaluation parameter described below and the adjustment parameter used for the adjustment of the intensity of the light emitted from the illumination apparatus 11. The correlation may be determined in advance through experiments or simulations. The correlation will be described in detail below.

The controller 31 includes, for example, a specialized micro-processor, or a general-purpose CPU configured to perform a specific function by reading a specific program. The controller 31 performs overall control of the image processing apparatus 13.

For example, the controller 31, via the communication interface 29, acquires the captured image subjected to the post-stage image processing by the imaging apparatus 12.

The controller 31, on the basis of brightness of the captured image, determines a size of the pupil of the subject 18, i.e., a level of ambient light inside the car 16. The following is a further detailed description of this determination.

The controller 31 detects the eye of the subject 18 in the captured image. For the detection of the eye, any technique including techniques which use pattern matching or techniques for extraction of characteristic features of the captured image may be employed.

The controller 31 extracts a predetermined region of the captured image that includes the eye (the pupil) of the subject 18.

Figure 4A:
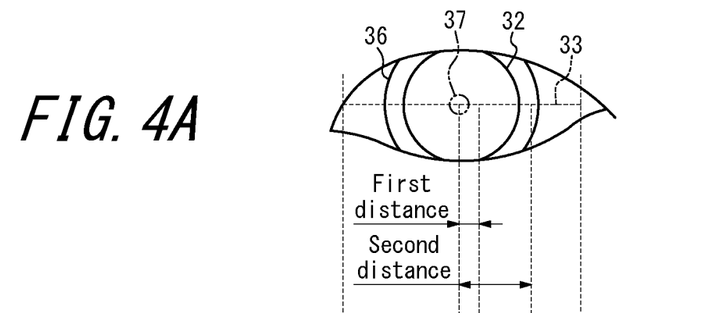
FIGS. 4A and 4B are diagrams illustrating an eye of a driver in a captured image and brightness when the level of light inside the vehicle is low.
Figure 4B:
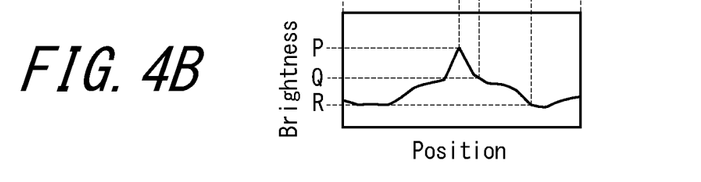

FIG. 4A illustrates the eye of the subject 18 in the captured image captured during nighttime or the like when the ambient light inside the car 16 is at a relatively low level. Due to the low level of light inside the car 16, the pupil 32 is relatively large in relation to an iris 36 (a black area). FIG. 4B is a graph illustrating a relation between the brightness and positions on a line 33 that passes through the center of the pupil 42 of the subject 18 within the predetermined region in the captured image. The horizontal axis represents the position, and the vertical axis represents the brightness. As described above, the captured image is the image of the pupil brightly illuminated according to the present embodiment. Thus, the pupil 32 is bright in the captured image. Within the predetermined region of the captured image, a first brightness P at the center (a first position) of the pupil 32 has the highest brightness. A central portion 37 of the pupil 32 substantially corresponds to a peak of the brightness as illustrated in FIG. 4B. A second brightness Q at a position (a second position) at a predetermined distance (at a first distance) from the first position is relatively high but is lower than the first brightness P. A third brightness R at a position (a third position) at a predetermined distance (at a second distance) longer than the first distance from the first position is relatively low due to its position in the iris 36 outside the pupil 32 and is lower than the second brightness Q.

Figure 5A:
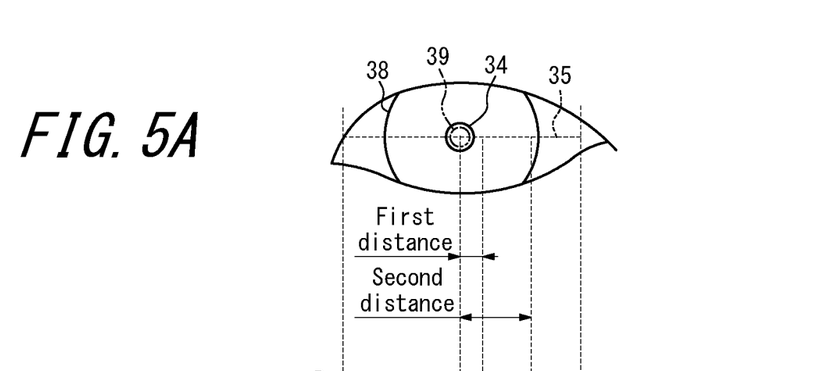
FIGS. 5A and 5B are diagrams illustrating the eye of the driver in the captured image and the brightness when the level of light inside the vehicle is high.
Figure 5B:
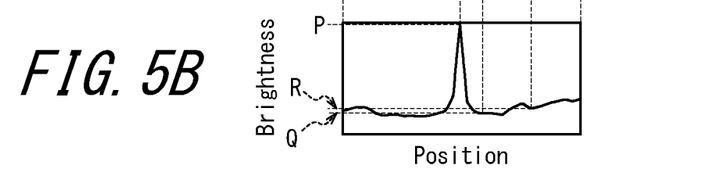

On the other hand, FIG. 5A illustrates the eye of the subject 18 in the captured image captured during daytime or the like when the level of the ambient light inside the car 16 is relatively high. Due to the high level of light inside the car 16, a pupil 34 is relatively small in relation to an iris 38 in the captured image. FIG. 5B is a graph illustrating a relation between the brightness and positions on a line 35 that passes through the center of the pupil 34 of the subject 18 within the predetermined region of the captured image. The horizontal axis represents the position, and the vertical axis represents the brightness. Within the predetermined region of the captured image, the first brightness P of the center (a first position) of the pupil 34 has the highest brightness. A central portion 39 of the pupil 34 substantially corresponds to a peak of the brightness illustrated in FIG. 5B. The second brightness Q at a position (a second position) at a predetermined distance (at a first distance) from the first position is relatively low and lower than the first brightness P. The third brightness R at a position (a third position) at a predetermined distance (at a second distance) longer than the first distance from the first position is relatively low due to its position in the iris 38 outside the pupil 34 and substantially equal to the second brightness Q.

As described above, the pupil increases its size when the level of ambient light inside the car 16 is low, thereby resulting in the second position in the captured image being within the pupil 32 (see FIG. 4A) and consequently the second brightness Q is relatively high. On the other hand, the pupil decreases its size when the level of ambient light inside the car 16 is high, thereby resulting in the second position being outside the pupil 34 and within the iris 38 (see FIG. 5A) and consequently the second brightness Q is relatively low.

According to the present embodiment, the controller 31 scans the predetermined region of the captured image and detects the first position with the highest brightness, the first brightness P at the first position, the second position, and the second brightness Q at the second position. The controller 31 may further detect the third position and the third brightness R at the third position. The controller 31 calculates the evaluation parameter correlated with the size of the pupil, on the basis of the first brightness P and the second brightness Q. The controller 31 may calculate the evaluation parameter on the basis of the first brightness P, the second brightness Q, and the third brightness R.

For example, the evaluation parameter may be, but is not limited to, a difference P-Q between the first brightness P and the second brightness Q, a ratio Q/P of the second brightness Q to the first brightness P, or a ratio (P-Q)/(P-R) of the difference between the first brightness P and the second brightness Q to a difference between the first brightness P and the third brightness R.

The controller 31 determines the size of the pupil of the subject 18, i.e., the level of the ambient light inside the car 16, on the basis of the evaluation parameter calculated as described above. For example, when the ratio Q/P of the second brightness Q to the first brightness P is used as the evaluation parameter, the controller 31 determines that, as the Q/P is closer to 1, the pupil is larger and the level of ambient light inside the car 16 is lower. When the difference P-Q between the first brightness P and the second brightness Q is used as the evaluation parameter, the controller 31 determines that, as P-Q is smaller, the pupil is larger and the level of ambient light inside the car 16 is lower.

When the controller 31 detects the eye of the subject 18 in the captured image employing any appropriate technique as mentioned above, the controller 31 may also detect a size of the eye and, on the basis of the detected size of the eye, determine the first distance and the second distance. In particular, the controller 31 sets the first distance and the second distance to be longer, as the detected size of the eye is larger. Alternatively, the controller 31 sets the first distance and the second distance by multiplying the detected size of the eye (e.g., a length of the eye in a vertical direction) by a predetermined ratio. In this way, when the size of the eye (the pupil) of the subject 18 in the captured image varies in accordance with the distance between the subject 18 and the imaging apparatus 12 inside the car 16, variation in the relative lengths of the first distance and the second distance in relation to the size of the eye may be prevented. Thus, the size of the pupil, i.e., the level of ambient light inside the car 16, is more accurately determined than, for example, a configuration that uses fixed values for the first distance and the second distance.

The controller 31 determines the adjustment parameter corresponding to a calculated evaluation parameter on the basis of the information (see FIG. 3) stored in the memory 30 indicating the correlation between the evaluation parameter and the adjustment parameter used for the adjustment of the intensity of the light emitted from the illumination apparatus 11. In the correlation, as the size of the pupil determined on the basis of the evaluation parameter is larger, i.e., as the level of ambient light inside the car is lower, it is associated with an adjustment parameter for further reducing the intensity of the light emitted from the illumination apparatus 11.

For example, when the ratio Q/P of the second brightness Q to the first brightness P is used as the evaluation parameter and the duty ratio of the control signal for the illumination apparatus 11 is used as the adjustment parameter, as the ratio Q/P is larger (closer to 1), the duty ratio used as the adjustment parameter is set to be smaller. When the size of the pupil is large and thus it is determined that the level of ambient light inside the car 16 is low, the probability that a state of the subject 18 is determined with sufficient accuracy using a relatively low intensity of light emitted from the illumination apparatus 11 is high. In this case, the intensity of the light emitted from the illumination apparatus 11 is reduced, thereby decreasing the power consumption of the light source 19 of the illumination apparatus 11. As a result, the lifetime of the light source 19 may be extended, and a burden on the eye of the subject 18 caused by the light from the light source 19 may be eased.

On the other hand, when the controller 31 cannot detect the eye or the pupil of the subject 18 in the captured image such as when the first position in the captured image cannot be detected due to an insufficient intensity of the light emitted from the illumination apparatus 11, the controller 31 sets the adjustment parameter to increase the intensity of the light emitted from the illumination apparatus 11. In particular, when the controller 31 cannot detect the first position in the captured image, the controller 31 increases the duty ratio used as the adjustment parameter.

The controller 31 generates the adjustment information that includes information specifying a value of the adjustment parameter and outputs the adjustment information to the illumination apparatus 11 via the communication interface 29. Alternatively, the controller 31 may generate the adjustment information that includes a control signal corresponding to the adjustment parameter and outputs the adjustment information to the illumination apparatus 11 via the communication interface 29.

On the basis of the result of the detection of the eye or the pupil of the subject 18 in the captured image, the controller 31 generates control information for causing the warning apparatus 14 to generate a warning. For example, when the eye or the pupil of the subject 18 is not detected in the captured image for a predetermined time period, the subject 18 is likely to be looking away or falling asleep at the wheel. In this case, the controller 31 generates control information for causing the warning apparatus 14 to generate a warning. The controller 31 outputs the control information to the warning apparatus 14 via the communication interface 29.

The warning apparatus 14 may include, for example, a speaker or a vibrator. Upon receiving the control information from the image processing apparatus 13, the warning apparatus 14 generates a warning to the subject 18. The warning may be at least one of a sound and a vibration.

Figure 6:
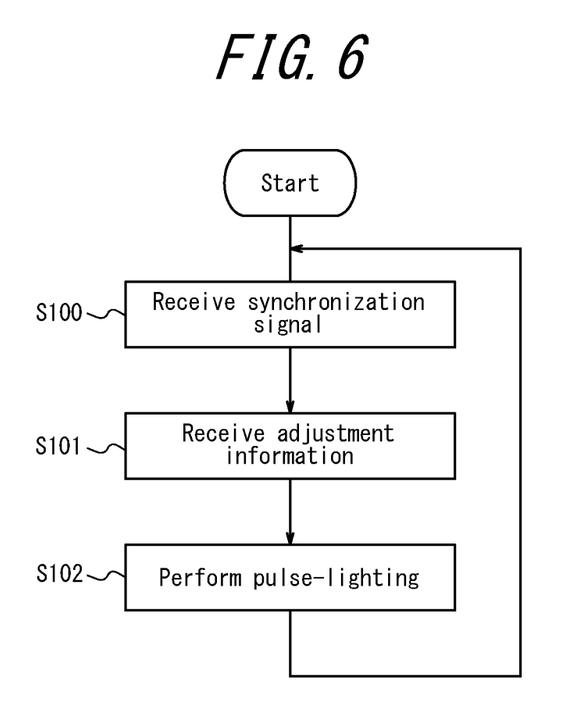
FIG. 6 is a flowchart illustrating operation of an illumination apparatus of FIG. 1.

Referring to a flowchart in FIG. 6, operation of the illumination apparatus 11 will be described. This operation starts, for example, when the car 16 starts moving, and repeats until a predetermined termination condition is met, such as when the engine is stopped.

At step S100, the illumination controller 22 acquires the synchronization signal from the imaging apparatus 12 via the communication interface 21.

At step S101, the illumination controller 22 acquires the adjustment information from the image processing apparatus 13 via the communication interface 21.

At step S102, by using the control signal generated on the basis of the adjustment information at step S101 or the control signal included in the adjustment information, the illumination controller 22 causes the light source 19 to perform the pulse-lighting. Then, the illumination controller 22 returns to step S100.

Figure 7:
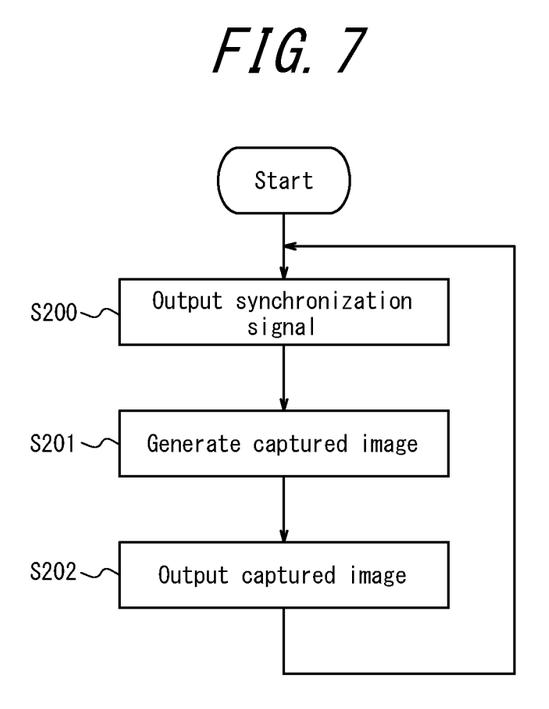
FIG. 7 is a flowchart illustrating operation of an imaging apparatus of FIG. 1.

Referring to a flowchart in FIG. 7, operation of the imaging apparatus 12 will be described. This operation starts when, for example, the car 16 starts moving, and repeats until a predetermined termination condition is met, such as when the engine is stopped.

At step S200, the camera controller 28 generates the synchronization signal indicating the timing for the imaging and outputs the synchronization signal to the illumination apparatus 11 via the communication interface 27.

At step S201, the camera controller 28 causes the image sensor 24 to capture the subject image and to generate the captured image.

At step S202, the camera controller 28 controls the image processer 26 and the communication interface 27 such that the captured image subjected to the post-stage image processing is output to the image processing apparatus 13 via the network 15. Then, the camera controller 28 returns to step S200.

Figure 8:
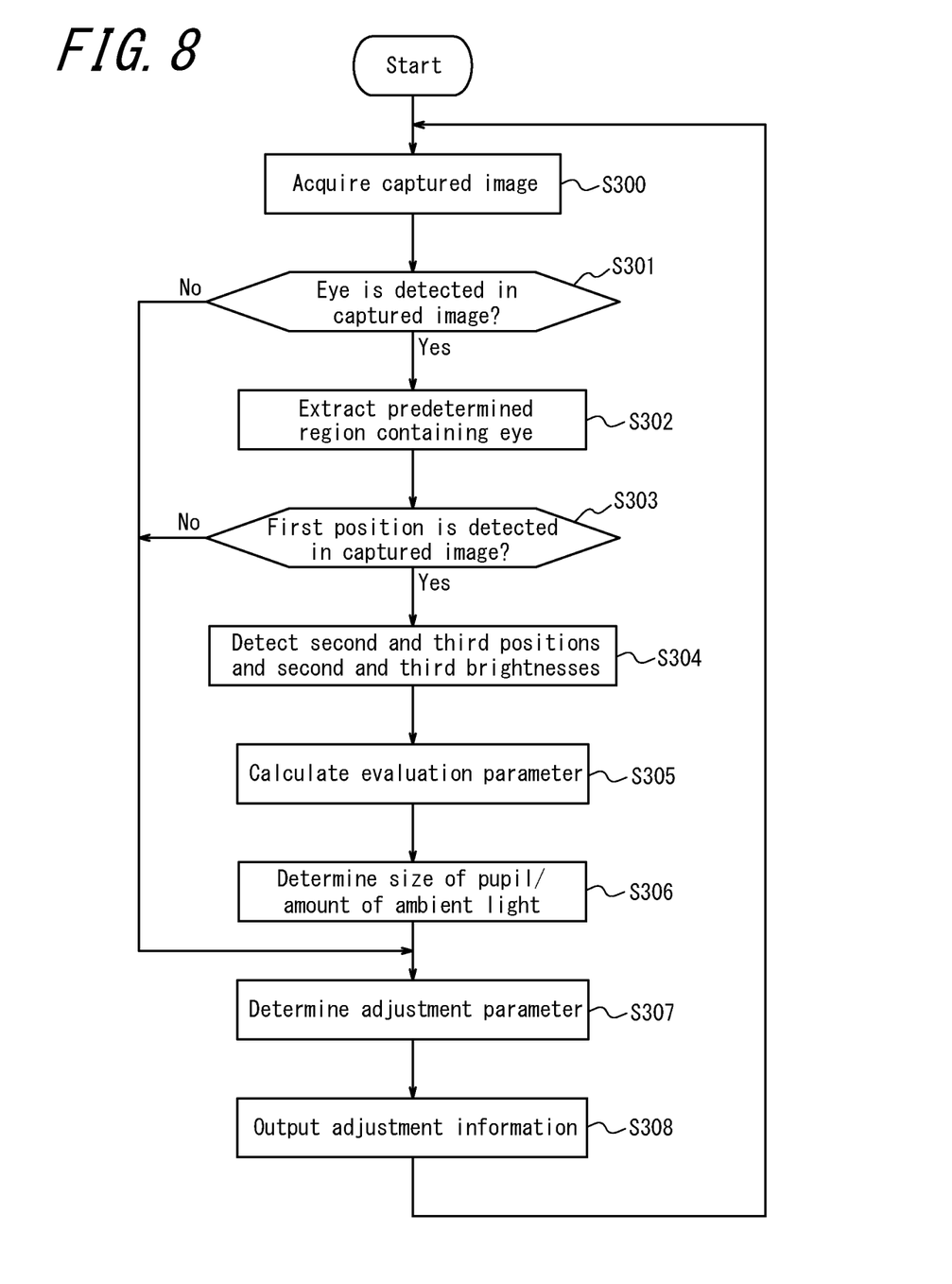
FIG. 8 is a flowchart illustrating operation of an image processing apparatus of FIG. 1.

Referring to a flowchart in FIG. 8, operation of the image processing apparatus 13 to output the adjustment information will be described. This operation starts when, for example, the car 16 starts moving, and repeats until a predetermined termination condition is met, such as when the engine is stopped.

At step S300, the controller 31, via the communication interface 29, acquires the captured image subjected to the post-stage image processing by the imaging apparatus 12.

At step S301, the controller 31 determines whether the eye of the subject 18 is detected in the captured image by employing, for example, the technique that uses the pattern matching or the technique for extraction of characteristic features of the captured image. When the eye is detected in the captured image (in the case of a Yes determination at step S301), the controller 31 proceeds to step S302. When the eye is not detected in the captured image (in the case of a No determination at step S301) the controller 31 proceeds to step S307.

At step S302, when the eye is detected in the captured image at step S301 (in the case of the Yes determination at step S301), the controller 31 extracts the predetermined region of the captured image that includes the eye of the subject 18.

At step S303, the controller 31 scans the predetermined region of the captured image and determines whether the first position with the highest brightness and the first brightness P at the first position are detected. When the first position and the first brightness P are detected (in the case of a Yes determination at step S303) the controller 31 proceeds to step S304. When the first position or the first brightness P are not detected (in the case of a No determination at step S303) the controller 31 proceeds to step S307.

At step S304, when the first position and the first brightness P are detected at step S303 (in the case of the Yes determination at step S303) the controller 31 detects the second position and the second brightness Q at the second position. The controller 31 may further detect the third position and the third brightness R at the third position.

At step S305, on the basis of the first brightness P and the second brightness Q, the controller 31 calculates the evaluation parameter correlated to the size of the pupil. The controller 31 may calculate the evaluation parameter on the basis of the first brightness P, the second brightness Q, and the third brightness R.

At step S306, on the basis of the evaluation parameter calculated, the controller 31 determines the size of the pupil of the subject, i.e., the level of ambient light inside the car 16.

At step S307, when the eye is not detected in the captured image at step S301 (in the case of the No determination at step S301), or when the first position or the first brightness P is not detected at step S303 (in the case of the No determination at step S303), the controller 31 sets the adjustment parameter in such a manner as to increase the intensity of the light emitted from the illumination apparatus 11. On the other hand, when the size of the pupil, i.e., the level of ambient light is determined at step S306, the controller 31 sets the adjustment parameter in such a manner as to further reduce the intensity of the light emitted from the illumination apparatus 11, as the size of the pupil is larger, i.e., as the level of ambient light inside the car 16 is lower.

At step S308, the controller 31 generates the adjustment information including the information specifying the value of the adjustment parameter and outputs the adjustment information to the illumination apparatus 11 via the communication interface 29. Alternatively, the controller 31 may generate the adjustment information including the control signal corresponding to the adjustment parameter and output the adjustment information to the illumination apparatus 11 via the communication interface 29. Then, the controller 31 returns to step S300.

Typically, the level of ambient light such as natural light entering the car varies depending on the conditions outside the car, i.e., daytime and nighttime. The ambient light includes light with various wavelengths. With conventional technologies, therefore, ambient light at a high level may cause noise and degrade accuracy in determination of the state of the subject. Under various conditions, emitting high intensity light from an illumination means for the purpose of securing a sufficient level of light may increase the power consumption of a light source of the illumination means. As such, there is room for improvement to reduce the power consumption of the light source.

On the other hand, the image processing apparatus 13 of the driver monitoring system 10 according to the present embodiment acquires the captured image of the subject 18 illuminated by the light from the light source 19. The image processing apparatus 13, on the basis of the size of the pupil of the subject 18 determined from the captured image, generates the adjustment information used for the adjustment of the intensity of the light from the light source 19. In this way, the intensity of the light from the light source is adjusted on the basis of the size of the pupil of the subject 18 that varies in accordance with the level of ambient light inside the car 16. Thus, unlike a configuration which emits light with a fixed intensity, the driver monitoring system 10 of the present embodiment enables a reduction in the power consumption of the light source 19 of the illumination apparatus 11, an extension of the life of the light source 19, and eases the burden on the eye of the subject 18 caused by the emitted light.

When the eye or the pupil of the subject 18 is not detected in the captured image, the image processing apparatus 13 generates the adjustment information to increase the intensity of the light. In this way, when the pupil is not detected due to the lack of the intensity of the light etc., the intensity of the light is increased making the pupil more likely to be detected. Thus, the state of the subject 18 may be more accurately determined.

The image processing apparatus 13 determines the size of the pupil on the basis of, within the predetermined region of the captured image that includes the pupil, the first brightness at the center of the pupil, i.e., at the first position where the brightness is maximum, and the second brightness at the second position at the first distance from the first position. In this way, the size of the pupil may be determined on the basis of the brightness at two positions in the captured image, thereby reducing the processing load compared to, for example, the processing load for techniques which determine the size of the pupil on the basis of brightness of the entire area corresponding to the eye of the subject 18 in the captured image.

The image processing apparatus 13 determines the first distance on the basis of the size of the eye detected in the captured image. In this way, the relative length of the first distance with respect to the size of the eye that is detected is prevented from varying between, for example, when the subject 18 is positioned near the imaging apparatus 12 and when the subject 18 is positioned remote from the imaging apparatus 12. Thus, the size of the pupil may be more accurately determined than in a configuration that uses a predetermined value for the first distance.

Although the present disclosure has been described on the basis of various figures and embodiments, it should be appreciated that various modifications and changes may be implemented by those who are ordinarily skilled in the art on the basis of the disclosure. Accordingly, such modifications and changes are included in the scope of the disclosure. For example, functions and the like included in each means or step may be rearranged without logical inconsistency, so as to combine a plurality of means or steps together or to separate them.

Figure 9:
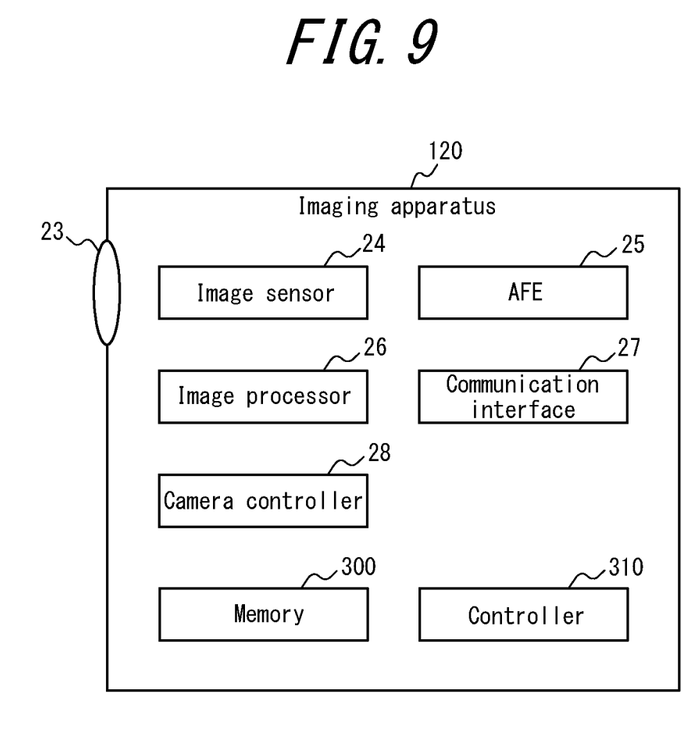
FIG. 9 is a block diagram schematically illustrating a configuration of an imaging apparatus according to another embodiment of the present disclosure.

For example, the driver monitoring system 10 according to the above embodiment includes the illumination apparatus 11, the imaging apparatus 12, the image processing apparatus 13, and the warning apparatus 14. However, the constituent elements and functions of the driver monitoring system 10 may be rearranged. For example, some or all of configurations and functions of the illumination apparatus 11, the image processing apparatus 13, and the warning apparatus 14 may be borne by the imaging apparatus 12. For example, as illustrated in FIG. 9, an imaging apparatus 120 that includes some of the configuration and functions of the image processing apparatus 13 according the above embodiment includes the imaging optical system 23, the image sensor 24, the AFE 25, the image processer 26, the communication interface 27, the camera controller 28, a memory 300, and a controller 310. The imaging optical system 23, the image sensor 24, the AFE 25, the image processer 26, the communication interface 27, and the camera controller 28 function similarly to those of the above embodiment. The memory 300 has a configuration and a function similar to the memory 30 of the image processing apparatus 13 of the above embodiment, and the controller 310 has a configuration and a function similar to the controller 31. For example, the controller 310, similarly to the controller 31, generates the adjustment information used for the adjustment of the intensity of the light from the light source on the basis of the size of the pupil of the subject determined from the captured image. The camera controller 28 and the controller 310 of the imaging apparatus 120 may be implemented by one or more processors.

Some of the constituent elements of the driver monitoring system 10 according to the above embodiment may be provided outside the car 16. For example, the image processing apparatus 13 may be implemented by a communication device such as a mobile phone or an external server and connected to other constituent elements of the driver monitoring system 10 in a wired or wireless manner.

The invention claimed is:

1. An image processing apparatus comprising:
an image acquirer configured to acquire a captured image capturing a subject illuminated by light from at least one light source; and
a controller configured to generate adjustment information for adjusting an intensity of the light from the at least one light source on the basis of a size of a pupil of the subject determined from the captured image,
wherein the controller is configured to detect a first position where brightness is maximum within a predetermined region of the captured image that includes the pupil, a first brightness at the first position, a second position at a first distance from the first position in the captured image, and a second brightness at the second position, and determine the size of the pupil on the basis of the first brightness and the second brightness.

2. The image processing apparatus according to claim 1, wherein the adjustment information causes the intensity of the light to be reduced as the size of the pupil determined increases.

3. The image processing apparatus according to claim 1, wherein the adjustment information causes the intensity of the light to be increased when an eye or the pupil of the subject is not detected in the captured image.

4. The image processing apparatus according to claim 1, wherein the adjustment information includes at least one of a control signal for causing the light source to perform pulse-lighting, information specifying a duty ratio of the control signal, a pulse width, a period, or a frequency, information specifying a value of a driving current of the light source, and information specifying a number of light sources to be caused to emit light.

5. The image processing apparatus according to claim 1, wherein the controller is configured to determine that the size of the pupil is larger as a difference between the first brightness and the second brightness is greater, or as a ratio of the second brightness to the first brightness is greater.

6. The image processing apparatus according to claim 1, wherein the controller detects a size of an eye of the subject in the captured image and determines the first distance on the basis of the size of the eye.

7. An imaging apparatus comprising:
an image sensor configured to generate a captured image by capturing a subject illuminated by light from a light source; and
a controller configured to generate adjustment information for adjusting an intensity of the light from the light source on the basis of a size of a pupil of the subject determined from the captured image,
wherein the controller is configured to detect a first position where brightness is maximum within a predetermined region of the captured image that includes the pupil, a first brightness at the first position, a second position at a first distance from the first position in the captured image, and a second brightness at the second position, and determine the size of the pupil on the basis of the first brightness and the second brightness.

8. A driver monitoring system comprising:
an illuminator configured to emit light to a driver of a vehicle;
an imager configured to generate a captured image by capturing the driver illuminated by the light; and
an image processor configured to generate adjustment information for adjusting an intensity of the light from the illuminator on the basis of a size of a pupil of the driver determined from the captured image,
wherein the image processor is configured to detect a first position where brightness is maximum within a predetermined region of the captured image that includes the pupil, a first brightness at the first position, a second position at a first distance from the first position in the captured image, and a second brightness at the second position, and determine the size of the pupil on the basis of the first brightness and the second brightness.

9. A vehicle comprising:
an illuminator configured to emit light to a driver;
an imager configured to generate a captured image by capturing the driver illuminated by the light; and
an image processor configured to generate adjustment information for adjusting an intensity of the light from the illuminator on the basis of a size of a pupil of a subject determined from the captured image,
wherein the image processor is configured to detect a first position where brightness is maximum within a predetermined region of the captured image that includes the pupil, a first brightness at the first position, a second position at a first distance from the first position in the captured image, and a second brightness at the second position, and determine the size of the pupil on the basis of the first brightness and the second brightness.

10. An image processing method comprising:
a step of acquiring a captured image capturing a subject illuminated by light from a light source; and
a step of generating adjustment information for adjusting an intensity of the light from the light source on the basis of a size of a pupil of the subject determined from the captured image,
wherein a first position is detected where brightness is maximum within a predetermined region of the captured image that includes the pupil, a first brightness at the first position, a second position at a first distance from the first position in the captured image, and a second brightness at the second position, and the size of the pupil is determined on the basis of the first brightness and the second brightness.

* * * * *